United States Patent [19]
Barbere

[11] Patent Number: 5,759,191
[45] Date of Patent: Jun. 2, 1998

[54] COAXIAL PTCA CATHETER WITH ANCHOR JOINT

[75] Inventor: Michael D. Barbere, Dunstable, Mass.

[73] Assignee: C. R. Bard, Inc., Murray Hill, N.J.

[21] Appl. No.: 171,343

[22] Filed: Dec. 22, 1993

Related U.S. Application Data

[63] Continuation of Ser. No. 27,930, Mar. 8, 1993, abandoned, which is a continuation of Ser. No. 771,861, Oct. 8, 1991, abandoned, which is a continuation of Ser. No. 395,785, Aug. 18, 1989, abandoned, which is a continuation of Ser. No. 375,572, Jul. 5, 1989, abandoned, which is a continuation of Ser. No. 371,990, Jun. 27, 1989, abandoned.

[51] Int. Cl.$^6$ ............................................. A61M 25/10
[52] U.S. Cl. .................................... 606/194; 604/96
[58] Field of Search ............................ 606/194, 192, 606/193, 195; 604/96–103; 128/772

[56] References Cited

U.S. PATENT DOCUMENTS

| | | |
|---|---|---|
| 3,543,759 | 12/1970 | McWhorter . |
| 4,323,071 | 4/1982 | Simpson et al. ............... 128/343 |
| 4,638,805 | 1/1987 | Powell . |
| 4,646,742 | 3/1987 | Packard et al. ............... 128/344 |
| 4,665,925 | 5/1987 | Millar ............................ 128/663 |
| 4,689,041 | 8/1987 | Corday et al. ................. 604/53 |
| 4,794,928 | 1/1989 | Kletschka .................... 606/194 |
| 4,955,895 | 9/1990 | Sugiyama et al. ............ 606/194 |
| 5,100,381 | 3/1992 | Burns ........................ 606/194 X |
| 5,129,887 | 7/1992 | Euteneuer et al. ............ 606/194 |

FOREIGN PATENT DOCUMENTS

| | | |
|---|---|---|
| 8401513 | 4/1984 | European Pat. Off. . |
| 0213752 | 11/1987 | European Pat. Off. . |
| 8804560 | 6/1988 | WIPO . |

OTHER PUBLICATIONS

Promotional Sheet for Probe Balloon–On–A–Wire™ Dilatation System, distributed by USCI Division, C.R. Bard, Inc., Jan. 1989.

*Primary Examiner*—Michael H. Thaler
*Attorney, Agent, or Firm*—Arthur Z. Bookstein

[57] ABSTRACT

A balloon dilatation catheter used for percutaneous transluminal coronary angioplasty includes a coaxial construction of an inner tube and an outer tube. The inner tube extends distally beyond the distal end of the outer tube. A dilatation balloon is mounted on the distal end of the catheter and is connected at its proximal end to the distal end of the outer tube and at its distal end to the distal end of the inner tube. The lumen of the inner tube is adapted to receive a guidewire and may permit pressure monitoring and liquid infusion. The annular inflation lumen is defined between the inner and outer tubes. The distal end of the outer tube extends into the balloon and is anchored directly to the inner tube. The balloon may be inflated and deflated through an annular inflation lumen defined between the inner and outer tubes, there being openings in the outer tube within the balloon to communicate the inflation lumen with the interior of the balloon. The catheter displays increased column strength and resistance to axial buckling and balloon bunching by reason of the secure connection between the distal end of the outer tube and the inner tube.

7 Claims, 1 Drawing Sheet

COAXIAL PTCA CATHETER WITH ANCHOR JOINT

RELATED APPLICATION

This application is a continuation of application Ser. No. 08/027,930 filed Mar. 8, 1993, now abandoned, which is a continuation of application Ser. No. 07/771,861 filed Oct. 8, 1991, now abandoned, which is a continuation of application Ser. No. 07/395,785 filed Aug. 18, 1989, now abandoned, which is a continuation of application Ser. No. 07/375,572 filed Jul. 5, 1989, now abandoned, which is a continuation of application Ser. No. 07/371,990 filed Jun. 27, 1989, now abandoned.

FIELD OF THE INVENTION

This invention relates to catheters and, particularly, to catheters of the type used in percutaneous transluminal coronary angioplasty.

BACKGROUND OF THE INVENTION

Percutaneous transluminal coronary angioplasty (PTCA) is a procedure by which a balloon catheter is inserted into and manipulated within a patient's coronary arteries to unblock an obstruction (a stenosis) in the artery. Typically, the catheter is about 150 cm long and is inserted percutaneously into the patient's femoral artery in the region of the groin. The catheter then is advanced upwardly through the patient's arteries to the heart where, with the aid of a guidewire, the catheter is guided into the coronary artery where it can be controlled to perform the angioplasty procedure.

In one type of PTCA catheter, the catheter has two lumens. One lumen, for inflation and deflation of the balloon, extends from a fitting at the proximal end of the catheter and opens distally into the interior of the balloon. The balloon is inflated with a liquid and is deflated by aspirating the liquid from the balloon through the inflation/deflation lumen. The second lumen extends from another fitting at the proximal end of the catheter through the catheter and is open at the distal tip of the catheter shaft. The second lumen is adapted to receive a guidewire, such as the steerable small diameter type of guidewire disclosed in U.S. Pat. No. 4,545,390 (Leary) issued Oct. 8, 1985.

In a typical procedure, the guidewire is preliminarily loaded into the catheter and the assembly is inserted into a previously percutaneously placed guide catheter that extends to the region of the patient's heart and terminates at the entrance to the coronary arteries. The assembly of the balloon angioplasty catheter and the steerable guidewire is advanced through the guide catheter to the entrance to the coronary arteries. The guidewire then is projected into the coronary arteries and is steered by manipulation from its proximal end, while being observed under a fluoroscope, until the guidewire passes through the stenosis in the artery. Once the guidewire is in place, the balloon dilatation catheter is advanced over the guidewire, being thus guided directly to the stenosis so as to place the balloon within the stenosis. Once so placed, the balloon is inflated under substantial pressure to dilate the stenosis.

The anatomy of coronary arteries varies widely from patient to patient. Often a patient's coronary arteries are irregularly shaped and highly tortuous. The tortuous configuration of the arteries may present difficulties to the physician in properly placing the guidewire and then advancing the catheter over the guidewire. A highly tortuous coronary anatomy typically will present considerable resistance to advancement of the catheter over the guidewire. With some types of catheter construction, the increased resistance may cause a tendency for portions of the catheter to collapse or buckle axially. For example, in a catheter having a shaft formed from inner and outer coaxial tubes and a balloon mounted to the distal ends of the tubes, there may be a tendency for the tubes to telescope when presented to an increased resistance. The telescoping of the tubes will tend to draw the ends of the balloon together slightly but sufficiently to permit the balloon to become bunched up as it is forced through the stenosis. The bunching up of the balloon makes it more difficult for the balloon to cross the stenosis. It is among the principal objects of the invention to provide an improved construction for a PTCA catheter, particularly a coaxial catheter, which reduces the tendency for the catheter to telescope and buckle and for the balloon to become bunched up under such axial loads.

SUMMARY OF THE INVENTION

The invention is embodied in a coaxial type of PTCA catheter in which the elongate catheter shaft is formed from an inner tube and a coaxial outer tube. The inner tube extends from the proximal end fully to the distal end of the catheter and terminates in an open distal outlet. The lumen extending through the inner tube serves as a guidewire lumen. The outer tube extends from the proximal end of the catheter and terminates short of the distal end of the inner tube. The dilatation balloon is mounted on the distal end of the catheter with its proximal end adhesively attached to the distal end of the outer tube and the distal end of the balloon being adhesively attached to the distal end of the inner tube. The annular lumen defined between the inner tube and the outer tube communicates with the interior of the balloon and serves as the inflation/deflation lumen.

The present invention is intended to resist the tendency for the inner tube of the catheter shaft to telescopically buckle or collapse within the outer tube when being pushed from its proximal end as the distal end of the catheter meets resistance in the coronary arteries. Such resistance typically is met when crossing a stenosis during the negotiation of tightly curved coronary arteries. By preventing such telescoping, the present invention is intended to resist a tendency for the thin walled balloon to become bunched as it is pushed through the stenosis. In accordance with the invention, the column strength of the catheter is improved, telescoping of the inner and outer tubes and bunching of the balloon is avoided in that the distal end of the outer tube is securely anchored to the inner tube at a location within the balloon, preferably adjacent the proximal end. By preventing telescoping of the inner and outer tubes, the axial distance between the ends of the balloon does not contract and bunching of the balloon is avoided. Openings are formed in the distal end of the outer tube, adjacent the point of attachment to the inner tube, to communicate the inflation/deflation lumen with the interior of the balloon. By anchoring the distal end of the outer tube to the inner tube and thereby increasing the column strength of the catheter, it has been found that relative axial motion and telescopic buckling of the inner tube within the outer tube is avoided when the distal end of the catheter meets substantial resistance to advancement, as when crossing a difficult stenosis or negotiating tightly curved coronary arteries.

It is among the objects of the invention to provide an improved PTCA catheter construction.

Another object of the invention is to provide a PTCA catheter having a coaxial construction in which there is a reduced tendency for the balloon to become bunched as it is advanced through a resisting stenosis.

Another object of the invention is to provide a PTCA catheter having a coaxial construction in which there is a reduced tendency of the inner tube of the catheter shaft to buckle or telescope within the outer tube when the catheter is advanced through a resisting coronary anatomy.

A further object of the invention is to provide a coaxial PTCA catheter in which the outer tube of the catheter shaft is attached, at its distal end, to the inner tube of the catheter shaft.

DESCRIPTION OF THE DRAWINGS

The foregoing and other objects and advantages of the invention will be appreciated more fully from the following further description thereof, with reference to the accompanying drawings wherein.

DESCRIPTION OF THE PREFERRED EMBODIMENT

Figure 1:
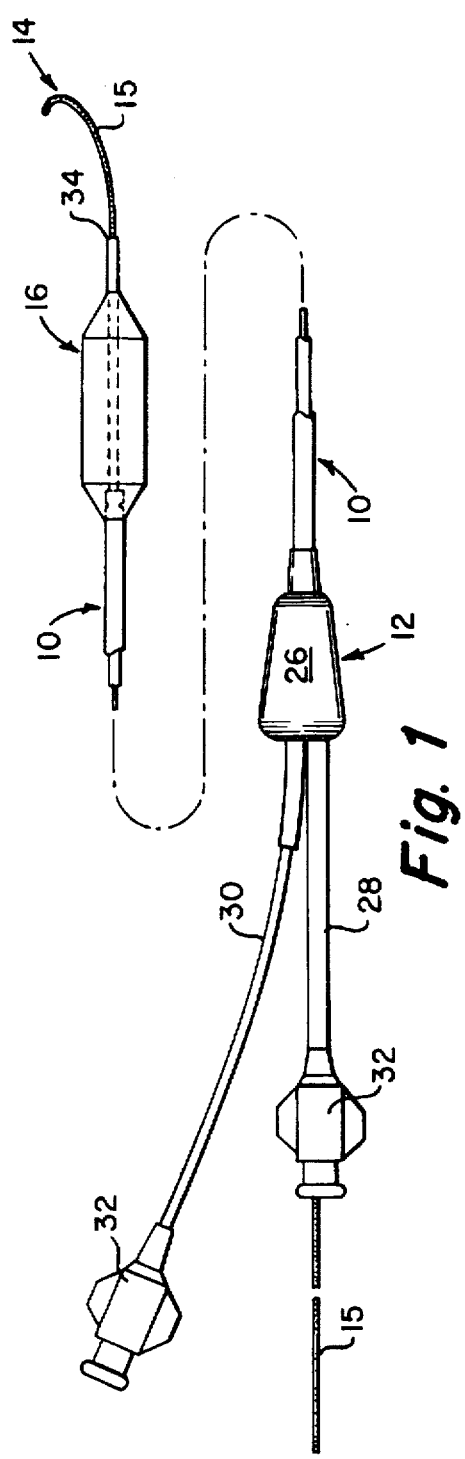
FIG. 1 is an illustration of a PTCA catheter of the type with which the invention may be employed.
Figure 2:
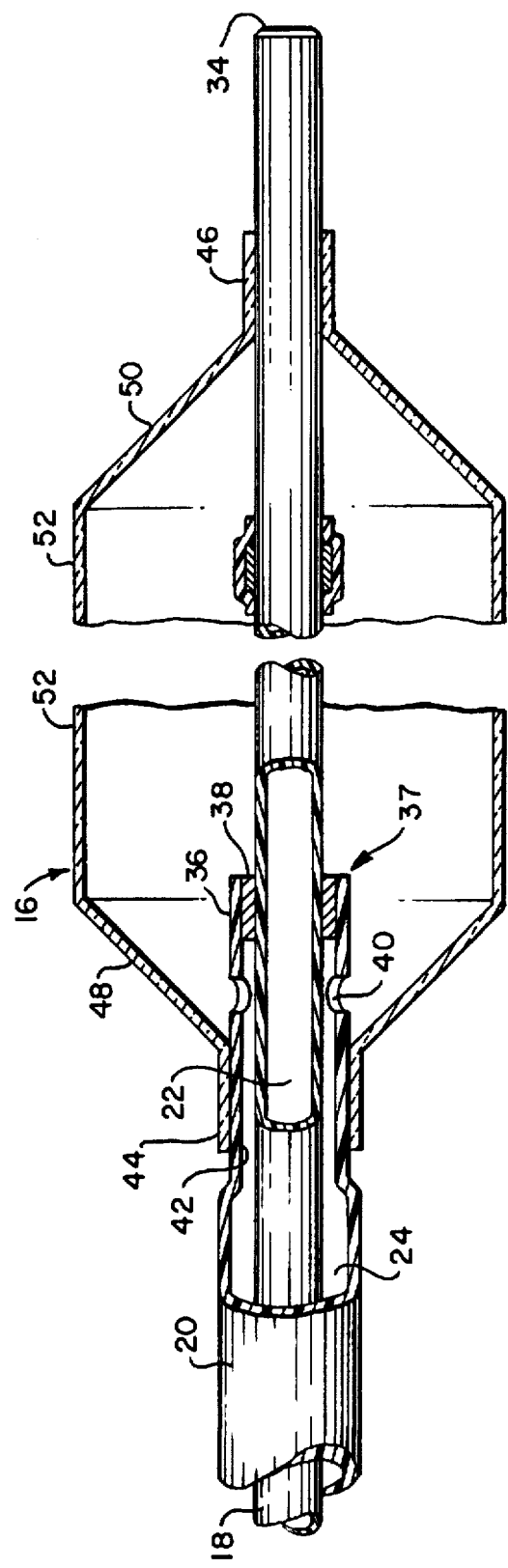
FIG. 2 is an enlarged cross-sectional illustration of the region of the catheter adjacent the proximal end of the balloon and illustrating the anchoring of the distal end of the outer tube of the catheter shaft to the inner tube of the catheter shaft.

As shown in FIG. 1, the catheter includes a shaft, indicated generally at 10. The catheter has a proximal end 12 and a distal end 14. A dilatation balloon 16 is mounted to the distal end of the shaft 10. In the illustrative embodiment of the invention, the catheter shaft 10 is formed from a pair of coaxial tubes, illustrated partly in enlarged detail in FIG. 2. The coaxial tubes include an inner tube 18 and an outer tube 20. The tubes 18, 20 may be formed from polyethylene, with the inner tube being formed, for example, from high density polyethylene and the outer tube being formed from linear low density polyethylene. By way of example, the catheter may be of the order of 150 cm long. The inner tube may have an outer diameter of about 0.027" and an inner diameter of 0.019", the wall thickness being of the order of 0.003". The outer tube 20 may have an outer diameter of the order of 0.045" and an inner diameter of the order of 0.035" with a wall thickness of the order of 0.005". The inner tube 18 defines an inner lumen 22 adapted to receive a guidewire, indicated generally in FIG. 1 at 15 with the proximal and distal ends of the guidewire 15 protruding from the proximal and distal ends of the catheter. The inner tube 18 extends fully to the distal tip of the catheter. An annular inflation lumen 24 is defined between the inner tube 18 and the outer tube 20.

The proximal end of the catheter is provided with a Y-fitting 26 which may be molded from an appropriate plastic and to which is connected a pair of flexible proximal tubes 28, 30. The Y-fitting 26 is formed so that the proximal tube 28 is in communication with the guidewire lumen 22 in the inner tube 18 and the proximal tube 30 is in communication with the annular inflation lumen 24. Each of the proximal tubes 28, 30 is provided with a fitting 32 at its proximal end by which appropriate fluid devices such as syringes, inflation devices or the like may be connected.

The guidewire lumen 22 extends from the proximal end of the catheter fully to the distal tip of the catheter and terminates in an outlet opening 34. Thus, the guidewire 15, which is longer than the catheter may be passed through the guidewire lumen 22 and may exit from the outlet tip 34, with the proximal end of the guidewire 15 protruding proximally from the proximal tube 28. The guidewire may be manipulated from its proximal end and may be steered through the coronary anatomy to the branch of the coronary arteries where the stenosis is located.

The outer tube 20 extends from the Y-fitting 26 to a location short of the inner tube 18 and terminates within the balloon 16. In accordance with the invention, and as described further below, the distal end 36 of the outer tube 20 is securely anchored to the inner tube 18 at a location within the balloon. A ring-like spacer 38 which also may be formed from polyethylene may be interposed in the annular region between the inner and outer tubes 18, 20. The distal end 36 of the outer tube 20 and spacer 38 may be secured to each other and to the inner tube 18 by an appropriate adhesive or by heat bonding the spacer 38 and inner and outer tubes together. A pair of circumferentially spaced (e.g., 180°) apertures 40 are formed in the outer tube within the balloon to communicate the inflation lumen 24 with the interior of the balloon so as to permit inflation and deflation of the balloon with an appropriate liquid as will be familiar to those skilled in the art.

The distal end of the outer tube 20 may be formed to define a reduced diameter portion 42 to which the proximal neck 44 of the balloon 16 may be adhesively attached. The distal end of the balloon is provided with a cylindrical distal neck 46 which is adhesively attached to the distal region of the inner tube 18. The balloon typically includes proximal and distal cone sections 48, 50 and a central cylindrical section 52, as will be appreciated by those skilled in the art. The balloon may be formed from a suitable material such as polyethylene terephthalate. It may be made in a manner described in U.S. Pat. No. 4,490,421 (Levy). The balloon may be adhesively attached to the inner and outer tubes by suitable adhesive such as an ultraviolet cured urethane adhesive.

The catheter may be provided with a small band 54 of highly radiopaque material such as gold, about the inner tube 18 within the region of the balloon in order to render the balloon region of the catheter visible under fluoroscopy. By way of example, the marker band 54 may be approximately 1 mm long and may have a wall thickness of the order of 0.002". It may be retained in place on the inner tube 18 by a heat shrunk encapsulating tube 56 of an appropriate plastic, such as a linear low polyethylene material.

From the foregoing, it will be appreciated that after the guidewire has been desirably placed in the patient's coronary anatomy, the physician will then advance the catheter over and axially along the guidewire. Should the coronary anatomy present resistance, as by presenting a narrow difficult stenosis and/or tortuous path, the increased column strength resulting from anchoring the distal end of the outer tube 20 to the inner tube 18 will increase the pushability of the catheter. The axial force applied to both the inner and outer tubes is available to push the catheter through the tortuous anatomy and/or the balloon through the difficult stenosis. With the foregoing arrangement, the tendency of the inner tube to telescopically buckle or collapse is avoided. As a consequence, the axial distance between the ends of the balloon is maintained and the balloon will not bunch up as it is pushed through a tight stenosis.

The invention thus provides an improved coaxial catheter construction for a PTCA catheter by which the column strength and resistance to telescopic buckling of the catheter, and particularly, of the inner tube and balloon of a coaxial catheter, is improved. The resulting catheter has increased pushability. Bunching up of the balloon is avoided. It should be understood, however, that the foregoing invention is intended merely to be illustrative thereof and that other embodiments and modifications may be apparent to those skilled in the art without departing from its spirit.

Having thus described the invention what I desire to claim and secure by Letters Patent is:

1. A two tube, two lumen coaxial balloon dilatation catheter comprising:

an elongate, flexible catheter shaft having a proximal region, a proximal end and a distal end, wherein the shaft is formed from an inner tube defining a guidewire lumen therethrough, and a surrounding outer tube coaxial with the inner tube and defining an annular inflation lumen therebetween, the inner tube being of smaller diameter than the outer tube and having a distal end region extending distally of the distal end of the outer tube;

an inflatable dilatation balloon having a proximal end and a distal end, the proximal end of the balloon being attached to the distal region of the outer tube, the distal end of the balloon being attached to the distal region of the inner tube at a distal connection;

the outer tube being attached to the inner tube at a location between the proximal region of the catheter shaft and said distal connection to resist axial telescoping of the inner tube with respect to the outer tube when the catheter is advanced against a resistance at the distal region of the catheter, the outer tube terminating proximally of said distal connection;

means for communicating the annular inflation lumen with the interior of the balloon to facilitate inflation and deflation of the balloon, the inflation lumen comprising the sole lumen in communication with the interior of the balloon; and means at the proximal end of the catheter for accessing each of the guidewire and inflation lumens.

2. A coaxial balloon dilatation catheter as defined in claim 1 wherein the distal end of the outer tube is attached to the inner tube at a location within the inflatable portion of the balloon.

3. A catheter as defined in claim 2 wherein the means communicating the inflation lumen with the interior of the balloon comprises at least one aperture associated with the outer tube for communicating the inflation lumen with the interior of the balloon.

4. A catheter as defined in claim 3 wherein a portion of the outer tube is disposed within the balloon and wherein the at least one aperture is formed in the portion of the outer tube that is disposed within the balloon.

5. A catheter as defined in claims 3 or 4 further comprising:

a tubular spacer interposed between the inner and outer tubes at the end of the inflation lumen, the tubular spacer being attached to each of the inner and outer tubes to define the point of connection of the inner and outer tubes.

6. A two-tube, two lumen coaxial balloon dilatation catheter as defined in claim 5 wherein the single inner tube is formed from a high density polyethylene and a single surrounding outer tube is formed from a linear low density polyethylene.

7. A two tube, two lumen coaxial balloon dilatation catheter as defined in any one of claims 1 or 2-4-6 wherein the single inner tube is formed from a high density polyethylene and the single surrounding outer tube is formed from a linear low density polyethylene.

* * * * *